United States Patent
De Matos Correia E Valle et al.

(10) Patent No.: US 7,507,548 B2
(45) Date of Patent: Mar. 24, 2009

(54) MULTIDIMENSIONAL DETECTION OF ABERRANT PHENOTYPES IN NEOPLASTIC CELLS TO BE USED TO MONITOR MINIMAL DISEASE LEVELS USING FLOW CYTOMETRY MEASUREMENTS

(75) Inventors: Alberto Orfao De Matos Correia E Valle, Salamanca (ES); Carlos Eduardo Pedreira, Rio de Janeiro (BR); Elaine Sobral Da Costa, Rio de Janeiro (BR)

(73) Assignee: University of Salamanca, Salamanca (ES)

( * ) Notice: Subject to any disclaimer, the term of this patent is extended or adjusted under 35 U.S.C. 154(b) by 529 days.

(21) Appl. No.: 10/791,994

(22) Filed: Mar. 3, 2004

(65) Prior Publication Data

US 2004/0224371 A1   Nov. 11, 2004

Related U.S. Application Data

(60) Provisional application No. 60/451,738, filed on Mar. 4, 2003.

(51) Int. Cl.
*G01N 33/574* (2006.01)
(52) U.S. Cl. .................... 435/7.23; 435/7.21; 435/7.24; 435/40.5; 435/287.2; 435/973; 436/10; 436/63; 436/64; 436/165; 436/172; 422/73; 422/82.08
(58) Field of Classification Search ................ 435/7.21, 435/7.23, 7.25, 40.5, 287.2, 287.3, 973; 436/519, 436/522, 10, 16, 17, 18, 56, 63, 64, 165, 436/172, 175, 819; 422/68.1, 82.07, 73, 422/82.08
See application file for complete search history.

(56) References Cited

U.S. PATENT DOCUMENTS

| | | | |
|---|---|---|---|
| 4,284,412 A | 8/1981 | Hansen et al. | |
| 4,727,020 A | 2/1988 | Recktenwald | |
| 5,047,321 A | 9/1991 | Loken et al. | |
| 5,137,809 A | 8/1992 | Loken et al. | |
| 5,627,037 A * | 5/1997 | Ward et al. | ................. 435/7.21 |
| 6,287,791 B1 | 9/2001 | Terstappen et al. | |
| 6,913,901 B2 * | 7/2005 | Orfao de Matos Correia e Vale | ............... 435/29 |

OTHER PUBLICATIONS

Nagler et al., Detection of Minimal residual disease (MRD) after bone marrow transplantation (BMT) by multi-parameter flow cytometry (MPFC), Medical Oncology 16: 177-187 (1999).*
Barrena, S. et al., "Aberrant expression of tetraspanin molecules in B-cell chronic lymphoproliferative disorders and its correlation with normal B-cell maturation," Leukemia (2005), vol. 19, pp. 1376-1383.

* cited by examiner

*Primary Examiner*—Gail R Gabel
(74) *Attorney, Agent, or Firm*—Collard & Roe, P.C.

(57) ABSTRACT

A method for detecting aberrant phenotypes expressed by neoplastic cells includes the steps of: 1) staining one or more normal/reactive samples and one neoplastic sample with multiple combinations of monoclonal antibodies, 2) measuring fluorescence emissions associated to the stained cells, 3) storing two independent list mode data files of information on light scatter and fluorescence characteristics of each cell, 4) creating new data files by mixing list mode data from the data file containing information the neoplastic sample into the data file containing information on the normal samples, 5) defining corresponding to normal cells and areas corresponding to empty spaces in normal/reactive samples that may be occupied by tumor cells in neoplastic samples, 6) identifying events corresponding to neoplastic cells and events corresponding to normal cells coexisting in a multidimensional space, and 7) establishing the most relevant phenotypic aberrations displayed by the neoplastic cells as compared to their normal counterpart.

32 Claims, No Drawings

MULTIDIMENSIONAL DETECTION OF ABERRANT PHENOTYPES IN NEOPLASTIC CELLS TO BE USED TO MONITOR MINIMAL DISEASE LEVELS USING FLOW CYTOMETRY MEASUREMENTS

CROSS-REFERENCE TO RELATED APPLICATIONS

This application claims the benefit of Provisional Application Ser. No. 60/451,738 filed Mar. 4, 2003.

BACKGROUND OF THE INVENTION

1. Field of the Invention

This invention relates to the field of flow cytometry and more particularly to the sequential detection of aberrant patterns of protein expression on neoplastic cells and the identification of minimal numbers of neoplastic cells present among a major population of normal cells from blood, bone marrow, spinal fluid and lymph node samples. The invention enables: 1) the unequivocal identification of the aberrant phenotypes carried by neoplastic cells that allow their sensitive and specific identification, 2) the estimation of their utility for the identification of minimal numbers of neoplastic cells displaying an identically aberrant phenotype in another sample from the same individual obtained simultaneously or subsequently, and 3) the calculation of the distribution of neoplastic cells in blood, bone marrow, spinal fluid and lymph node samples both in terms of the percentage of cells and the number of cells per microliter of sample, by means of multiparameter flow cytometry analysis of the cells present in a sample stained with multiple combinations of monoclonal antibodies mixed with a quantified microbead (microparticle) suspension.

2. Background of the Invention

In U.S. Pat. No. 5,047,321, Loken and Terstappen described the multiparameter analysis of cellular components in a body fluid. The body fluids described included blood and bone marrow. Using a combination of two nucleic acid dyes, a fluorescently labeled monoclonal antibody and two light scatter parameters, Loken and Terstappen were able to discriminate among various cellular components of blood and bone marrow, count the number of cells within each component and provide a differential analysis of each of them. Through the combined staining with the LDS-751 (Exciton) DNA-dye, the thiazol orange (TO, Molecular Probes, Inc) RNA-dye and a fluorescently labeled anti-CD45 monoclonal antibody, together with the measurement of forward and sideward light scatter on whole blood and bone marrow aspirates, these authors were able to identify and differentiate between, nucleated red cells, erythrocytes, reticulocytes, platelets, lymphocytes, monocytes, neutrophil granulocytes, basophilic granulocytes, eosinophilic granulocytes and precursors of all nucleated cells. However they could not show the ability of this approach to specifically differentiate between normal and neoplastic cells, coexisting in the same sample.

In U.S. Pat. No. 6,287,791, Terstappen and Chen describe a further refinement of the U.S. Pat. No. 5,047,321, but they did not show any better characterization of the different leukocyte populations.

In U.S. Pat. No. 5,137,809, Loken and Sha describe the multiparameter analysis of cellular components in bone marrow. The authors describe the use, in a first step, of a combination of monoclonal antibodies each labeled with a different fluorochrome, to stain all leukocytes and of further combinations to stain selected populations of leukocytes, in a second step.

All the methods described above were able to identify several populations of normal leukocytes present in blood and bone marrow samples and were only identifying selected subpopulations as identified by the specific combination of monoclonal antibodies and nucleic acid dyes used; nevertheless, they were not able to provide an approach for the specific and reproducible identification of neoplastic cells admixtured naturally or artificially with normal cells in a sample. Also these approaches allow enumeration of the subpopulations of normal leukocytes identified in terms of percentage of total leukocytes. Moreover, by using these methods it is not possible to easily link and directly compare the information on the amount of light scatter and fluorescence measured for cells contained in a first sample to that of cells containing in a second different sample, especially if they derive from different tissues from the same individual, from different individuals or if they have been measured under different conditions.

In U.S. Pat. No. 5,627,037, Ward et al propose a one step technique for the calculation of the number of one or more cell populations contained in a given volume of a blood sample. This approach employs a mixture of reagents containing a mixture of one or more cell markers, a fluorescent quantified microparticle and a fixative. The technique described by Ward et al allows the calculation of the absolute counts of leukocytes, such as CD4+ T-cells, but does not provide any specific indication of the exact procedures to be applied for the enumeration of individual subpopulations of blood leukocytes.

In the last decade many different reports have been published which show that neoplastic cells from a great majority of patients suffering from hematological malignancies display aberrant patterns of antigen expression as detected through the use of several triple and quadruple combinations of monoclonal antibodies analyzed by flow cytometry (Reviewed in Vidriales et al. Best Clin Res Pract, 2003; 16:599-612). These abnormal patterns of antigen expression are never detected in normal cells and they include one or more of the following subtypes: 1) cross-lineage antigen expression, 2) asynchronous antigen expression, 3) antigen over- and under-expression, 4) abnormally high or low light scatter properties, and 5) ectopic phenotypes. Based on these abnormalities several disease-type specific panels of three- and four-color combinations of monoclonal antibody reagents have been proposed for the systematic identification of leukemic cells expressing aberrant phenotypes, in virtually every patient with precursor B-acute lymphoblastic leukemia (BCP-ALL; Lucio et al, Leukemia, 2001; 15: 1185-1192), T-ALL (Porwit-MacDonald, Leukemia, 2000; 14: 816-825), acute myeloblastic leukemia (AML; San Miguel et al, Blood, 2001; 98: 1746-1751), B-cell chronic lymphocytic leukemia (Rawstrom et al, Blood 2001; 98: 29-35) and other B-cell chronic lymphoproliferative disorders (Sanchez et al, Leukemia, 2002; 16: 1460-1469), among other diseases.

In all the approaches described so far for the identification of aberrant phenotypes expressed by neoplastic cells, data interpretation is carried out by an experienced person, with extensive knowledge on the patterns of protein expression on normal cells. Through this approach it has been shown that neoplastic cells from patients studied at first diagnosis and at relapse frequently show more than one aberrant phenotype, especially if relatively large panels of combinations of three or four monoclonal antibodies are used for their identification. Based on all the aberrant phenotypes detected at diagnosis, new 3- or 4-color combinations of monoclonal antibodies for the specific investigation of these neoplastic cell-specific phenotypes are designed and tested for their further use for the investigation of minimal infiltration by neoplastic cells in other samples obtained concurrently (e.g. for staging purposes) or subsequently (e.g. for monitoring the disease and the therapy). However, the need for data interpretation by an expert person with a high amount of knowledge and experience on the patterns of protein expression differentially observed in normal versus neoplastic cells, makes the identification of aberrant phenotypes subjective and difficult to reproduce. Moreover, many of these aberrant phenotypes are only present in a subset of all leukemic cells present in a given sample and they may change in the same patient, and even in another sample from the same tissue, with time. This further makes the identification of aberrant phenotypes, apart from being subjective, uncertain, with potentially occurring false negative and positive results. In addition, current knowledge about the phenotypes of normal cells from blood, bone marrow, spinal fluid and lymph nodes occurring at frequencies of less than $10^{-4}$ is very limited; this impacts negatively in the sensitivity of these approaches for detecting minimal numbers of neoplastic cells among a majority of normal blood and bone marrow cells which under the best technical and biological conditions, is currently of between $10^{-3}$ (detection of one neoplastic cells among 1000 normal cells) and $10^{-6}$ (one neoplastic cell in one million normal cells) depending on the exact lineage, type and maturation stage of the neoplastic cells, the aberrant phenotype used for the identification of the neoplastic cells, and the type of specimen studied.

DESCRIPTION OF THE INVENTION

The present invention relates to a new method to improve the sensitivity, specificity and reproducibility of the detection of aberrant phenotypes expressed by neoplastic cells present in bone marrow, peripheral blood, spinal fluid and lymph nodes.

The invention comprises the steps of: 1) separately stain one or more normal/reactive samples and one neoplastic sample with identical or at least partially overlapping multiple combinations of monoclonal antibodies, each monoclonal antibody in each combination being conjugated to a different fluorochrome and each combination of monoclonal antibodies having in common at least three fluorochrome conjugated monoclonal antibodies, 2) sequentially measure the fluorescence emissions associated to large numbers of cells stained with each of the combinations of monoclonal antibodies from the normal/reactive samples and the neoplastic sample, using flow cytometry, 3) store two independent list mode data files each containing information on the specific light scatter and fluorescence characteristics of each individual cell analyzed, one containing information corresponding to the cells from the normal/reactive samples and the other containing information corresponding to cells from the tumor sample, 4) create new data files by mixing, at known proportions, list mode data on cellular events from the data file containing information about the cells present in the neoplastic sample into the data file containing information on the cells present in the normal samples, 5) define in a multidimensional space generated by the flow cytometric measurements of light scatter and fluorescence emissions, those areas occupied by events corresponding to normal cells and those areas corresponding to empty spaces in normal/reactive samples and that may be occupied by tumor cells in neoplastic samples, 6) sequentially identify in the new merged data files those events corresponding to neoplastic cells and those events corresponding to normal cells in a multidimensional space generated by the flow cytometric measurements of light scatter and fluorescence emissions, 7) establish the most relevant phenotypic aberrations displayed by the neoplastic cells as compared to their normal counterpart, that allow their unequivocal and clear sensitive and specific identification of those events corresponding to the neoplastic cells contained in the merged data file. This procedure simulates dilutional experiments of neoplastic cells in a normal sample through the use of computational procedures and could be used by mixing the information either directly from two or more distinct data files or after adjusting the relative position of the populations of cellular events measured according to pre-established standards.

As briefly described above, the first step of the method of this invention comprises staining of one or more normal/reactive samples and of one neoplastic sample with multiple combinations of at least four monoclonal antibodies, each monoclonal antibody in each combination being conjugated to a different fluorochrome and each combination having in common a subgroup of at least three fluorochrome conjugated monoclonal antibodies.

The normal and neoplastic samples are of one of the following types: blood, bone marrow, spinal fluid and lymph nodes.

The neoplastic samples may contain hematopoietic tumor cells or neoplastic cells from any non-hematopoietic origin such as breast cancer, renal carcinomas, prostate tumors, lung cancer, bladder carcinomas and gastric tumors, among others.

The neoplastic samples are obtained at first diagnosis, relapse and at any time period after diagnosis; they may contain high numbers of neoplastic cells or minimal disease. They might have been stained directly after obtained and after being culture in vitro.

The panel of combinations of monoclonal antibodies used to stain the neoplastic sample is identical to the panel of monoclonal antibody combinations used for the staining of the normal/reactive samples; alternatively the former panel can be shorter than the latter, but a part of the former panel is fully contained in the latter panel of combinations of monoclonal antibodies.

For each pair of panels used to stain normal/reactive and neoplastic samples, the clone of each monoclonal antibody reagent used in each individual combination of monoclonal antibodies, and the fluorochrome to which it is conjugated, are identical in the two panels of monoclonal antibody combinations.

The number of fluorescence components in each of the multiple combinations of monoclonal antibodies comprises at least four different fluorochromes, each linked to a different monoclonal antibody, whose fluorescence emission is distinguishable from that of the other fluorochrome-conjugated monoclonal antibodies. Fluorescence labels that can be used in the practice of this invention include fluorescein isothiocyanate (FITC), phycoerythrin (PE), peridin chlorophyll protein (PerCP), allophycocyanin, ALEXA FLUOR 488®, ALEXA 647®, pacific blue, ALEXA FLUOR 405®, cyanin 5 (Cy5), cyanin5.5(Cy5.5) and conjugates thereof coupled to PE, to APC or to PerCP (e.g. PE/Cy5, PE/Cy5.5, PE/Cy7, APC/Cy7 and PerCP/Cy5.5). Each monoclonal antibody is capable of recognizing a different antigen, which is expressed in different quantities on the various populations of leukocytes and on the populations of neoplastic cells in a sample. The exact monoclonal antibodies which are common to all combinations of monoclonal antibodies used to stain a pair of normal/reactive and neoplastic samples may vary depending on the type, the lineage and the maturation stage of the tumor cells of interest, contained in the neoplastic sample.

Once selected the panel of multicolor combinations of monoclonal antibodies to be used for staining purposes, the cells in a known volume of sample are mixed together with a lysing solution, a fluorescent micro-particle at known quantities and the mixture of monoclonal antibody reagents. For each of the multiple combinations of monoclonal antibodies used to stain a sample, a different aliquot containing a replicate of the sample mixed with a lysing solution, a fluorescent microparticle and the specific combination of monoclonal antibodies is used. After the nucleated cells are stained and the non-nucleated red cells are lysed, the sample can be washed and measured in a flow cytometer wherein the cells are passed one by one through one or more sensing regions, or it can be directly analyzed in a flow cytometer without mediating any washing step. Alternatively, the sample can be mixed together with only the monoclonal antibodies and a population of fluorescent microparticle and, once stained, measured directly in the flow cytometer.

The population of reference microparticles may be uniform or composed of multiple populations of microbeads of differing size, differing fluorescence amounts, density, shape, volume, adhesion characteristics and other physico-chemical properties. A population of microparticles may be composed of fluorescent particles, of microparticles whose surface is covered with anti-immunoglobulin antibodies or a mixture of both. In order to be able to calculate the absolute number of a population of cells present in a microliter of sample, a quantified population of microparticles in known numbers per volume of sample is added.

In each of the sensing regions of the flow cytometer, the cells and the microparticles are individually exposed to a source of light at a one or more wavelengths; for each stained cell in a sample of cells taken from blood, bone marrow, spinal fluid and lymph node and for each microparticle, at least two measures of light scatter are taken and at least four measures of fluorescence are taken. The information recorded for all light scatter and fluorescence measures of each individual cell and of each individual microparticle analyzed, is stored in a data storage and analysis device, such as a computer. Information for each sample aliquot analyzed containing microbeads and cells stained with a combination of monoclonal antibodies, can be stored in a separate data file; however, in a preferred embodiment of this invention, information on the microbeads and the cells stained with all combinations of monoclonal antibodies used to stain a sample is stored in a single file through sequential acquisition of information on each separate aliquot of the sample/microparticle mixture stained with a different combination of monoclonal antibodies; specific identification of those events corresponding to each aliquot stained with a different combination of monoclonal antibodies that have been sequentially measured may be attained through the use of a parameter such as "time of acquisition". In any case, data on the normal/reactive samples and on the neoplastic sample are stored separately in different data files. In U.S. Pat. No. 4,284,412 and in U.S. Pat. No. 4,727,020, the configuration and the use of a typical flow cytometer instrument equipped with a data storage computer system and with a single and a double light source are described, respectively. In these systems, data is usually stored in a list mode FCS (flow cytometry standard) format. In this format, information for each individual event is listed for all parameters measured in a sequential way according to the sequence at which each cell and microparticle was measured in the flow cytometer.

If information from a single sample is contained in independent data files—each of the data files containing information on the light scatter and fluorescence characteristics of those events corresponding to a mixture of microparticles and cells stained with a specific combination of monoclonal antibodies—information from all data files corresponding to the multiple combinations of monoclonal antibodies with which the sample has been stained, is merged into a single data file. In every data file resulting from merging the data contained in two or more different data files, the information corresponding to each individual data file merged is ordered in a separate list before or after the list mode data containing information on the events of the other data files with which it has been merged.

A data file containing information about cells from normal/reactive samples that have been measured in a flow cytometer may be composed of information obtained after merging multiple data files corresponding to an identical number of sample aliquots each stained with a different combination of monoclonal antibodies, all of which correspond either to one single normal/reactive sample or to multiple normal/reactive samples. A data file resulting from merging the information collected for two or more normal/reactive samples, each stained separately with an identical panel of multiple combinations of monoclonal antibodies, is composed of normal/reactive samples from randomly selected individuals, from individuals from a well-defined age interval or from any other group of individuals defined according to their age, gender, and underlying non-neoplastic conditions, among other characteristics.

For the identification of the aberrant phenotypes expressed by neoplastic cells which have been stained with a specific panel of multiple combinations of monoclonal antibodies, new data files are generated by mixing at well known ratios data corresponding to cellular events from the data file containing information about the cells present in the neoplastic sample into the data file containing information on the cells present in the normal/reactive samples. In the merged data file containing information on cellular events from both the neoplastic sample and the normal/reactive samples, events corresponding to each of the two data files are ordered one after the other in a list mode data format and they may be labeled differently in any multidimensional space generated by the flow cytometric measurements of light scatter and fluorescence emissions, using software tools (e.g. dots painted in different colors).

If data files containing information on the light scatter and fluorescence characteristics of cells from multiple different samples are merged, and they have been acquired under different conditions (e.g. distinct instrument settings), in different flow cytometry instruments or at different times (e.g. in different days, months or years), the relative position of each cellular event in the multidimensional space formed by all parameters measured (light scatter and fluorescence emissions), is adjusted automatically by software operations based on the relative changes observed in the position of the populations of internal reference microparticles measured simultaneously with the cells, for each of the samples. After adjusted, the normalization process is controlled because the corrected position of those events corresponding to the microparticles and to identical populations of normal/reactive cells contained in the multiple samples merged, overlaps.

Different data files containing information about cellular events measured in one or more normal samples and one neoplastic sample may be generated. For that purpose all the information corresponding to the whole cellularity measured in the neoplastic sample or different parts of it corresponding to the whole information measured in variable numbers of randomly selected events representative of the neoplastic cells present in this file are added to the information of the data file obtained after measuring normal/reactive samples. This procedure simulates dilutional experiments of neoplastic cells in a normal sample through the use of computational procedures. Accordingly, serial dilutions of data about individual events of for instance 1/1, 1/10, 1/100, 1/1000, 1/10000, 1/100000, 1/100000, and 1/10000000 (events/events) can be created by merging data from a file corresponding to normal/reactive samples with data from a file corresponding to a neoplastic sample.

Once the data files from normal/reactive samples and from a neoplastic sample have been merged into a single data file, the neoplastic cells present in this new merged data file are identified using software tools, as those populations of at least 15 events falling into the spaces that remain empty in the initial file containing only information on the cells of the normal/reactive samples. By quantifying the amount of light scatter and fluorescence measured for each individual population of neoplastic cells as compared to those populations of normal cells stained with identical panels, statistical information on the most discriminant aberrant phenotypes displayed by the neoplastic cells can be derived. Each aberrant phenotype may be composed of a combination of two or more light scatter and fluorescence measures and it allows the unequivocal, sensitive and specific identification of those events corresponding to the neoplastic cells present in the merged data file as being different from all populations of events corresponding to normal/reactive cells contained in the same merged data file.

The procedure of this invention could also be used to detect abnormal patterns of antigen expression to monitor cell activation and a cell function.

DETAILED DESCRIPTION OF THE PREFERRED EMBODIMENT

The invention will be illustrated by an example which does not limit its areas of application as follows:

EXAMPLE 1

1.—Samples:

Five mL of peripheral blood (PB) was obtained by venipuncture from 10 healthy volunteers and placed in VACUTAINER™ (Becton Dickinson, New Jersey, N.J.) tube containing EDTA as anticoagulant. In addition 5 mL of a PB sample from a patient diagnosed with B-cell chronic lymphocytic leukemia (B-CLL) with an absolute lymphocytosis of $5 \times 10^9$/L were also obtained.

2.—Sample Preparation:

After gentle mixing the sample, 200 uL of each PB sample containing between $10^6$ and $2 \times 10^6$ nucleated cells was placed in six different replicate tubes and washed for 5 minutes at 540 g with 2 mL/tube of phosphate buffered saline. Then, to each tube from each PB sample one of the following five-color combinations of monoclonal antibodies was added, each monoclonal antibody conjugated with a different fluorochrome (FITC/PE/PE-Texas red/PerCP-Cy5.5/APC) being added at saturating amounts in a volume of 5 uL: 1) CD22/CD23/CD19/CD45/CD5, 2) CD43/CD79b/CD19/CD45/CD5, 3) anti-Lambda/anti-kappa/CD19/CD45/CD5, 4) anti-IgM/CD27/CD19/CD45/CD5, 5) CD11c/CD10/CD19/CD45/CD5, 6) CD103/CD25/CD19/CD45/CD5 and, 7) CD20/Zap70/CD19/CD45/CD5. After gently mixing the samples were incubated for 15 minutes at room temperature in the darkness. After this incubation, 200 uL of a microbead suspension (PerfectCOUNT, Cytognos, Salamanca, Spain), containing $2 \times 10^3$ microbeads was added to each replicate tube.

3.—Data Acquisition:

After gentle mixing the light scatter and fluorescence of the stained cells were measured in a FACSARIA flow cytometer (Becton/Dickinson Biosciences BDB-, San José, Calif.) equipped with two emission laser lights tuned at 488 and 635 nm using the FACS DIVA (BDB) software. For each sample analyzed a single data file was collected which contained information on the forward (FSC) and sideward light scatter (SSC), and the fluorescence emissions of FITC, PE, PE-texas red, PE-Cy5.5 and APC for each cell and microbead analysed. In addition information corresponding to the time (of acquition parameter) was also recorded. For each sample acquisition was performed for the different tubes in the sequence defined in the above section about "sample preparation" using CD45-associated red fluorescence as threshold. For each combination, information on 500.000 CD45+ cells was acquired. Acquisition was stopped between two consecutive tubes for 10 seconds.

4.—Data Manipulation and Data Analysis:

Prior to data analysis, list mode data contained in all the 10 files corresponding to the 10 normal PB samples was merged in an ordered way from sample 1 to sample 10 in a single data file. For that purpose data corresponding to the measures of FSC, SSC, FITC, PE, PE-Texas red, PE-Cy5.5 and APC fluorescence emission for each microbead and cellular event was introduced into a data base after being transformed into channel values (scaled from 0 to 2048) using the alphaFACS assistant 1.1a software (University of Stanford, Stanford, Calif.).

An algorithm was then built based on the data from the normal sample using the Lymphogram B software (Version: beta-test, Cytognos, Salamanca, Spain) to identify through clustering analysis, all different populations of normal cells identified with the common parameters measured for all sample aliquots (FSC, SSC, CD19, CD45, CD5) as well as the microparticles measured in each sample aliquot. Statistical data of each cell population for each measured parameter was then used to estimate the multi-dimensional probability distribution function, e.g. by using Parzen windows (Duda R. O. et al., Pattern Classification, John Wiley & Sons 2001). One or more prototypes (codebook vectors) are set to be the representatives of each population of cells and microbeads present in the data file collected for normal samples.

In parallel, a similar analysis was performed with the B-CLL datafile. The estimated distribution of the Perfect-Count microbead particles obtained in the B-CLL data file was then compared to the position obtained in the Normal datafile. In the B-CLL the microbeads gave an identical distribution but in a distinct position in the space $R^7$, shifts of different magnitude being observed in each dimension. Based on the shifts observed a correction function was applied and the position of all events in the B-CLL datafile was adjusted according to this function. After adjusted the new values for the events corresponding to the distribution of the populations of normal residual CD5+/CD45++/CD19 T-cells and of normal residual CD45+/SSChigh neutrophils coexisting with the neoplastic B-CLL cells were calculated in the B-CLL datafile and compared with those obtained for the same normal populations present in the Normal datafile. The distribution of both populations of events was identical in both data files (p>0.05). Then, the multi-dimensional statistical data of all cellular and microbead populations, including the neoplastic B-cell population was used to build up one or more prototypes and to estimate probability distribution function of the population of neoplastic B-CLL cells, in addition to those corresponding to the normal residual populations of cellular events present in the same data file.

After this step, a copy of the data file containing information on the 10 normal PB samples (NORMAL data file) was merged at different proportions with data corresponding to events from the B-CLL data file after adjusting the values for the position of each event from this datafile as described above. The following dilution factors of events from the datafile corresponding to the adjusted B-CLL datafile into the NORMAL data file were done: 99/1, 1/1, 1/10, 1/100, 1/1000, 1/10000, 1/100000, 1/1000000, 10000000 (NORMAL/B-CLL data files. Then, clustering analysis was performed for the merged NORMAL/B-CLL data files as described above. In all NORMAL/B-CLL data files, a population of CD5+/CD19+/CD45 high/CD20 low/CD11c–/CD22–/CD23++/CD43+/CD79b low/IgM low/CD27+/CD103–/CD25 low/kappa low/lambda–/ZAP70–/CD10– neoplastic B-cells, which was absent in the NORMAL data file, was identified. From the other populations, the most closely related one was represented by normal CD5+/CD19+/CD45 high B-cells. This latter population could be clearly distinguished from the former based on the combination of CD20, CD22, CD79b, CD43, CD5 and CD25 (markers that would define the aberrant phenotype of the neoplastic B-CLL cells).

Accordingly, while only a few embodiments of the present invention have been shown and described, it is obvious that many changes and modifications may be made thereunto without departing from the spirit and scope of the invention.

What is claimed is:

1. A method for the identification of aberrant phenotypes expressed by neoplastic cells comprising the steps of:
   a) separately staining one or more normal/reactive samples and one neoplastic sample with overlapping multiple combinations of monoclonal antibodies, each monoclonal antibody in each combination being conjugated to a different fluorochrome and each combination having in common at least three fluorochrome conjugated monoclonal antibodies that are specific for tumor cells of interest contained in said neoplastic samples;
   b) sequentially measuring at least two light scatter emissions and the at least four fluorescence emissions of each stained cell from the normal/reactive samples and the neoplastic sample, using flow cytometry;
   c) storing two independent list mode data files, one containing measurement information on the specific light scatter and fluorescence characteristics of each cell analyzed from the normal/reactive samples in step b) and the other containing measurement information on the specific light scatter and fluorescence characteristics of each cell analyzed from the neoplastic sample in step b);
   d) creating new data files from step c) by merging, at known proportions cellular events from the data file containing measurement information about the cells present in the neoplastic sample from step b) into the data file containing measurement information on the cells present in the normal/reactive samples from step b);
   e) defining in a multidimensional space generated by the flow cytometric measurements of light scatter and fluorescence emissions from preestablished standards, those areas occupied by events corresponding to normal cells and those areas corresponding to empty spaces in normal/reactive samples and that may be occupied by tumor cells in neoplastic samples;
   f) sequentially identifying in the data files containing measurement information about the cells present in the neoplastic sample and merged as described in step d), those events corresponding to neoplastic cells as those populations of events contained in the neoplastic sample which fall into the empty spaces identified in the multidimensional space generated by the flow cytometric measurements of light scatter and fluorescence emissions from pre-established standards in step e); and
   g) establishing and identifying the phenotypic aberrations displayed by the neoplastic cells as compared to their normal counterpart, as those combinations of flow cytometric measurements of light scatter and fluorescence emissions from the events corresponding to the neoplastic cells contained in the merged data file from step d), that provide their identification and distinction from those events corresponding to cells from normal/reactive samples contained in the same merged data file from step d).

2. The method of claim 1, wherein the samples comprise peripheral blood.

3. The method of claim 1, wherein the samples comprise bone marrow.

4. The method of claim 1, wherein the samples comprise spinal fluid.

5. The method of claim 1, wherein the samples comprise lymph node.

6. The method of claim 1, wherein more than one randomly selected normal sample is stained.

7. The method of claim 1, wherein more than one normal sample is stained, all normal samples being selected from a well defined age group of individuals, or from any other group of individuals defined according to their gender and underlying non-neoplastic conditions.

8. The method of claim 1, wherein the neoplastic samples contain hematopoietic tumor cells of one or more different types.

9. The method of claim 1, wherein the neoplastic samples contain non-hematopoietic tumor cells of one or more different types.

10. The method of claim 1, wherein the neoplastic samples contain both hematopoietic neoplastic cells and non-hematopoietic tumor cells.

11. The method of claim 1, wherein the neoplastic samples are obtained at first diagnosis, relapse and at any time period after diagnosis.

12. The method of claim 1, wherein the neoplastic samples may contain high or minimal numbers of neoplastic cells.

13. The method of claims 1, wherein the samples are stained ex vivo, directly at blood collection.

14. The method of claim 1, wherein the samples are stained after being cultured in vitro.

15. The method of claim 1, wherein the panels of multiple combinations of monoclonal antibodies used to stain neoplastic samples and normal/reactive samples are identical.

16. The method of claim 1, wherein the panel of multiple combinations of monoclonal antibodies that is contacted to the neoplastic samples is in consonance for each labeled monoclonal antibody contained in said combinations of monoclonal antibodies, with the panel of combinations of monoclonal antibodies used to stain the normal/reactive samples, but with the inclusion of more labeled monoclonal antibodies into the cocktail that is subjected to contact with the normal/reactive samples.

17. The method of claim 1, wherein for each pair of panels of combinations of monoclonal antibodies, an exact clone of each monoclonal antibody used in each individual combination of monoclonal antibodies, and a fluorochrome to which it is conjugated, are identical in the two panels of combinations of monoclonal antibodies.

18. The method of claim 1, wherein the number of labeled monoclonal antibodies contained in each combination is composed of four or more different labeled monoclonal antibody reagents.

19. The method of claim 1, wherein the number of labeled monoclonal antibody reagents in common for all said combinations, is of three or more different labeled monoclonal antibodies.

20. The method of claim 1, wherein the exact monoclonal antibodies that are common to all combinations of monoclonal antibodies used in a panel to stain a pair of normal/reactive samples and a neoplastic sample may vary depending on the type, the lineage and the maturation stage of the tumor cells contained in the neoplastic sample.

21. The method of claim 1, wherein at least four different fluorochromes are used, each being conjugated to a different monoclonal antibody, a fluorescence emission of each fluorochrome being distinguishable from that of the other fluorochrome-conjugated monoclonal antibodies.

22. The method of claim 21, wherein a combination of compatible fluorochromes is selected from the group consisting of fluorescein isothiocyanate (FITC), phycoerythrin (PE), peridin chlorophyll protein (PerCP), allophycocyanin, Alexa Fluor 488®, Alexa 647®, pacific blue, ALEXA FLOUR 405®, cyanin 5 (Cy5), cyanin5.5(Cy5.5) and conjugates thereof coupled to PE, to APC or to PerCP (PE/Cy5, PE/Cy5.5, PE/Cy7, APC/Cy7 and PerCP/Cy5.5) and any additional fluorochrome.

23. The method of claim 1, wherein information from two distinct data files is merged directly without any correction.

24. The method of claim 1, wherein information from two different data files is merged after adjusting a relative position of populations of cellular events measured according to pre-established standards.

25. The method of claim 1, wherein the pre-established standards are reference microparticles.

26. The method of claim 25, wherein population of reference microparticles is uniform.

27. The method of claim 25, wherein a population of reference microparticles is composed of multiple populations of microbeads of differing size, density, volume, shape, amount of fluorescence, adhesion characteristics or other physicochemical properties.

28. The method of claim 25, wherein a population of microparticles is composed of fluorescent particles.

29. The method of claim 25, wherein a population of microparticles is composed of microparticles that have anti-immunoglobulin antibodies coated or immobilized on their surface.

30. The method of claim 25, wherein a population of microparticles is that have anti-immunoglobulin antibodies coated or immobilized on their surface.

31. The method of claim 25, wherein the microparticles are added in known numbers.

32. The method of claim 25, wherein serial dilutions of events from a data file corresponding to a neoplastic sample stained with a panel of monoclonal antibody combinations into a data file containing information on the light scatter and fluorescence measures of cells contained in one or more normal/reactive samples stained with an identical panel of monoclonal antibodies, are made to evaluate the sensitivity at which a small number of events corresponding to neoplastic cells could be detected once diluted at predefined known proportions with cellular events from a data file corresponding to a normal/reactive sample.

* * * * *